United States Patent [19]

Auer et al.

[11] Patent Number: 5,151,243
[45] Date of Patent: Sep. 29, 1992

[54] METALLURGICAL VESSEL

[75] Inventors: Johann Auer, St. Florian; Wilfried Pirklbauer, Niederneukirchen; Norbert Ramaseder; Hellmuth Smejkal, both of Linz, all of Austria

[73] Assignee: Voest-Alpine Industrieanlagenbau G.m.b.H, Linz, Austria

[21] Appl. No.: 795,996

[22] Filed: Nov. 22, 1991

Related U.S. Application Data

[62] Division of Ser. No. 595,587, Oct. 11, 1990, Pat. No. 5,096,165.

[30] Foreign Application Priority Data

Oct. 14, 1989 [DE] Fed. Rep. of Germany ....... 3934340

[51] Int. Cl.⁵ ............................................. C21C 5/46
[52] U.S. Cl. ...................................... 266/78; 266/45; 266/79; 266/272
[58] Field of Search ................... 266/45, 271, 272, 79, 266/78

[56] References Cited

U.S. PATENT DOCUMENTS 4,010,936 3/1977 Takashima .......................... 266/271
4,791,978 12/1988 Fishler ................................ 266/272

Primary Examiner—Melvyn J. Andrews
Attorney, Agent, or Firm—Hopgood, Calimafde, Kalil, Blaustein, & Judlowe

[57] ABSTRACT

There is disclosed a metallurgical vessel, such as a steelworks converter, having a refractory brick lining and a probe opening passing a wall of the vessel for introducing a measuring and/or sampling probe. In order that the probe opening will get obstructed only minimally, if at all, and possible deposits of slag will be removed easily and quickly, the probe opening is provided with a lining of graphite or a graphite/alumina mixture.

16 Claims, 4 Drawing Sheets

METALLURGICAL VESSEL

This application is a division of 07/595,587 field Oct. 11, 1990, now U.S. Pat. NO. 5,096,165.

This invention relates to a metallurgical vessel, in particular a steelworks converter, comprising a refractory brick lining and a probe opening passing a wall of the vessel for introducing a measuring and/or sampling probe.

BACKGROUND OF THE INVENTION

A converter of this kind is known from EP-B-0 079 290. The probe opening is to enable the rapid introduction of a probe for the purpose of taking a sample or for the purpose of temperature measurement or any other parameter measurement. A separate opening for the probe is suitable, in particular, if the mouth of the converter is difficult to accede.

The refractory brick lining of a steelworks converter, as a rule, consists of magnesite bricks such that the probe opening passing through the wall of the converter has an internal wall formed by such magnesite bricks. In practice, it has proved that probe openings of this type grow together or close up every now and then, because of slag deposits thereon which form particularly stable compounds with the magnesite bricks. Such deposits can be removed by boring the probe opening, yet this frequently involves damage to the brick lining of the metallurgical vessel and also requires much time. Since, however, measurements are to be carried out as quickly as possible, the difficulty feasible cleaning of the probe opening prior to carrying out any measurement is particularly disadvantageous.

OBJECT OF THE INVENTION

The invention aims at avoiding these disadvantages and difficulties and has as its object to provide a metallurgical vessel of the initially defined kind, whose probe opening is obstructed only minimally, if at all, possible deposits of slag being easily and quickly removable.

SUMMARY OF THE INVENTION

In accordance with the invention, this object is achieved in that the probe opening is provided with a lining of graphite or of a graphite/alumina mixture.

It has proved that slag adheres to graphite only with difficulty and that possible slag deposits can readily be removed, e.g., by a hand scraper.

Suitably, the inner end of the lining of the probe opening at least reaches into a region of the fractory brick lining having a temperature of about 1200° C. The slag used in the production of steel solidifies below approximately 1200° C. such that the graphite or graphite/alumina mixture is to be provided in a manner projecting from the exterior to a region having at least this temperature.

Advantageously, the inwardly projecting end of the lining of the probe opening maximally reaches into a region of the refractory brick lining having a temperature of about 1300° C. Since the slag is liquid above approximately 1200° C., the slag automatically will flow off the brick lining in regions of the refractory brick lining in which temperatures lying above these values are attained such that magnesite bricks will do in these regions. In order to save material and to avoid high-temperature stresses on the graphite or graphite/alumina mixture, the lining according to the invention should not extend too far into the interior of the vessel.

According to a preferred embodiment, the lining is designated as a pipe, thus rendering the installation especially simple.

In order to ensure a good fit of the pipe and hence a long service life of the same, the internal-side or inwardly extending and end of the pipe advantageously is supported on a shoulder of a refractory lining brick of the metallurgical vessel.

In order to account for axial movements of the pipe, which are temperature-dependent or due to movements of the brick lining material, without the pipe getting destroyed, the external-slide or the outwardly extending end of the pipe advantageously is supported relative to the shell of the metallurgical vessel by means of a refractory ramming mass. The probe opening preferably extends outwardly through a socket connected to the outer shell of the metallurgical vessel.

Since graphite usually reacts with oxygen and oxygen is present in excess at a steelworks converter during the blowing procedure, the probe opening suitably is closable by a lid at the end of socket. In this way, the access of air from outside and the penetration of oxygen from inside through the probe opening a swell as adverse effects on the graphite lining caused thereby are prevented. In addition, the lid has the advantage of preventing flames and flue gases from getting outside through the probe opening.

Suitably, the lid is pivotably fastened to the shell of the metallurgical vessel, for example, at the end of the socket the lid advantageously being actuatable by means of a pressure medium cylinder.

In order to ensure the closure of the lid during pivotal movements of the converter, the lid suitably is fixable by means of a locking device, which, suitably, is actuatable also by a pressure medium cylinder.

A preferred embodiment is characterized in that the pipe extends approximately over the entire length of the probe opening as far as to the interior of the metallurgical vessel and is assembled of two or more pipe sections, whose ends facing each other are provided with front an end surfaces at least partially overlapping each other in end to end contact in the direction transverse to the longitudinal axis. The configuration of the pipe in several sections allows for movements of the brick lining material transverse to the axis of the probe opening without causing a rupture of the pipe and a lateral offset of the parts resulting from rupture. Such a lateral offset of a pipe section impairs the introduction of the probe through the probe opening.

With the preferred embodiment of the pipe described above, displacements of the brick lining materials, such as of the working lining—whose displacements are the largest at the internal wall of the vessel—merely cause a pivotal movement of a pipe section relative to the consecutive pipe section, which results in a slight buckling of the axis; yet, one pipe section is reliably prevented from getting offset relative tot he other, which would create a step within the probe opening impeding the entering movement of the probe.

Due to the pipe reaching as far as to the interior of the metallurgical vessel, the possible deposition of slag at the transition from graphite to magnesite bricks, which would have to be removed prior to introducing a probe, is prevented.

A particularly suitable embodiment is characterized in that the front or end faces are designed as envelope of cone areas whose generatrices enclose an angle of between 30° and 60°, preferably of 45°, with the longitudinal axis. In other words, the ends are conically bevelled, one end being a female bevel which mates with a male bevel of the other end.

In this case, the envelope of cone areas of two facing end parts of the pipe sections have equal angles of aperture, the tips of the cones forming the envelope of cone areas being directed towards the interior of the metallurgical vessel. Thereby, a high degree of mobility of the pipe sections relative to one another is ensured and a gap possibly forming between the pipe sections will not impair the introduction of a probe due to the inclination of the gap in the direction towards the interior of the metallurgical vessel.

In order to perfectly support and anchor the pipe sections in the refractory lining of the metallurgical vessel, the pipe section located next to the internal space of the metallurgical vessel advantageously is provided with an annular bead or flange on its external side, which forms a supporting shoulder.

Preferably, the pipe sections have cylindrical internal spaces, the internal diameter of a pipe section arranged nearer to the interior of the metallurgical vessel being dimensioned larger than the internal diameter of a pipe section located further outwards towards the socket, thus rendering a slight offset of a pipe section, or a change in the inclination of a pipe section, with respect to the adjacent pipe section irrelevant to introducing the probe.

Suitably, the difference between the internal diameters of one pipe section and the consecutive or coaxially extending pipe section ranges between 1 and 3 cm, preferably amounts to about 2 cm.

According to a further embodiment of the invention, the probe opening will be kept free of slag by providing a stopper of graphite or a graphite/alumina mixture to be inserted into the probe opening and fixed in the inserted position.

Preferably, the inner stopper end at least projects into a region of the refractory brick lining that has a temperature of about 1200° C. and at most projects into a region having a temperature of about 1300° C.

In order to enable the simple manipulation of the stopper, the latter is fastened to a guide rod, on which a stop is provided at a distance from the stopper, which contacts the outer shell of the metallurgical vessel.

In order to be able to adapt the position of the stopper to different operational conditions, the stop advantageously is displaceable along the guide rod and fixable to the guide rod.

Suitably, the stop is designed as a lid, thus preventing the penetration of gas through the probe opening, which might occur on account of the play provided between the stopper and the probe opening.

In order to ensure the simple installation of the lid, the stop advantageously is provided with a centering projection on its side facing the interior of the metallurgical vessel.

For tiltable metallurgical vessels, the stop suitably is fixable to the shell of the metallurgical vessel by a locking device preferably actuatable by a pressure medium cylinder.

Advantageously, the guide rod is actuatable by means of a pressure medium cylinder such that no manipulations are required to lift and lower the stopper.

A preferred embodiment comprising a stopper is characterized in that the stopper extends over the entire length of the probe opening, its end facing the internal side of the metallurgical vessel suitably having a front face matching this internal side of the vessel.

By providing a stopper extending as far as to the internal side of the metallurgical vessel, the penetration of slag into the probe opening and a possible deposit of slag on the refractory lining of the probe opening are reliably prevented.

A stopper of this type offers particular advantages if the probe hole is to remain closed for an extended period of time. A stopper of refractory material would hardly be removable due to slag deposits forming between the stopper and the brick lining; brick lining material would break off, which, however, is prevented by the graphite stopper.

Advantageously, the outwardly projecting end of the stopper at the socket end is provided with a metal insert comprising a coupling means for coupling a stopper manipulation means thereto. The coupling means, for instance, may be designed as a bore having an internal thread into which thread a manipulation rod may be screwed.

Suitably, the metal insert comprises an annular bead overlapping the probe opening. This annular bead forms kind of a lid such that even the thin gap between the stopper and the probe opening is covered towards outside. At the same time, this bead or frange serves as a support for the stopper such that the latter will assume its correct position within the probe opening.

Preferably, the external diameter of the stopper is dimensioned to be smaller than the internal diameter of the probe opening by about 3 to 15%, in particular 5%.

According to a preferred embodiment in case a pipe of a graphite/alumina mixture is used, the latter is comprised of 60 to 85% graphite, the balance being $Al_2O_3$ and fireclay.

When using a stopper of a graphite/alumina mixture, it is comprised of 5 to 20% graphite, 30 to 70% $Al_2O_2$, the balance being fireclay.

The invention is based on the idea of providing graphite or a graphite/alumina mixture in the region of the probe opening in which slag is likely to deposit. In the case of a pipe-shaped graphite lining, the graphite region extends from a region of the brick lining in which the slag is sure to be liquid as far as to near the external-side end of the probe opening, if a stopper is provided, it suffices to make the internal stopper end, which reaches as far as into the above-mentioned region, of graphite or a graphite/alumina mixture.

With both variants, the refractory brick lining of the metallurgical vessel is worn as has hitherto been the case, yet without loosing its function to protect against slag deposits.

In the following, the invention will be explained in more detail by way of several exemplary embodiments and with reference to the accompanying drawings, wherein:

THE DRAWINGS

DETAILS OF THE INVENTION

Figure 1:
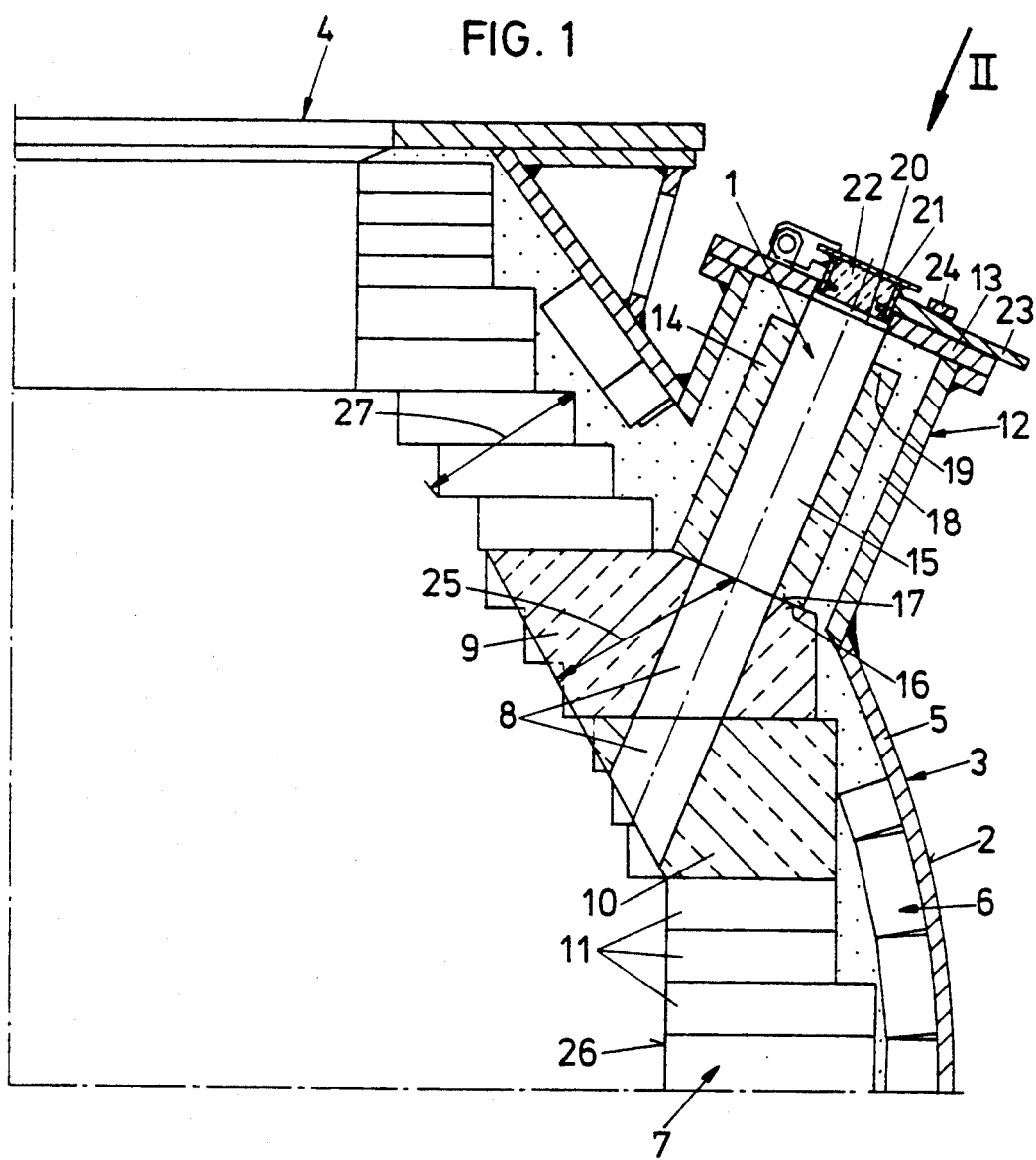
FIG. 1 is a partial section through a steelworks converter, whose plane of section is laid through the axis of rotation of the steelworks converter, according to a first embodiment.

According to the embodiment illustrated in FIG. 1, a probe opening 1 for introducing and removing a measuring and/or sampling probe passes the walls 2 of a metallurgical vessel 3, such as a steelworks converter, near its mouth 4. The wall 2 of the steelworks converter 3 is formed by a shell 5 of steel, on whose internal side a permanent lining 6 is provided. The permanent lining 6 is covered by a refractory working lining 7. In the region of the probe opening 1, the working lining 7 is formed by two bricks 9, 10 through which bore 8 extends and having dimensions larger than those of the neighboring lining bricks 11 of the working lining 7. All the bricks 9, 10, 11 of the working lining 7 are made of magnesite having the following composition:

MgO : 97%
$Al_2O_3$ : 0.1%
$Fe_2O_3$ : 0.2%
CaO : 1.9%
$SiO_2$ : 0.5%

In the region of the probe opening 1, a socket 12 of steel having a flange-like front plate 13 is welded to the shell 2 of the converter 3. A pipe 14 of graphite is arranged within said socket, the internal space 15 of the pipe being in alignment with the bore 8 passing through the two lining bricks 9, 10 of larger dimensions. The graphite pipe 14 is supported, by its inwardly projecting end 16, on a shoulder 17 of the upper 9 of the two lining bricks 9, 10 and is peripherally surrounded by a refractory ramming mass 18 filling the annular space between the shell of the socket 12 and the pipe 14. This ramming mass 18 also extends to or occupies the space between the external-side or outwardly extending end 19 of the pipe 14 and the front plate 13 of the socket 12. Thus, the pipe is capable of performing axial displacements that are temperature-dependent or caused by movements of the refractory brick lining 7, without being exposed to excessive pressure forces that might result in the destruction of the pipe 14. A central opening 20 in the front plate registers with the internal space 15 of the pipe 14.

The graphite pipe 14 has an external diameter corresponding to approximately twice the internal diameter, thus exhibiting a sufficiently large stability. The graphite pipe 14 need not be designed in one piece, but may also be comprised of several graphite rings superposed in the axial direction.

To the front plate 13 of the socket 12, a lid 21 is pivotably fastened. The lid is designed like a pot, its interior being lined with a refractory mass 22 and facing the interior of the converter. On the lid 21, there is provided a lateral projection 23 or lever allowing for the manual pivoting of the lid 21. This projection 23 may be overlapped by a locking device 24 attached to the front plate 13 of the socket 12 likewisely in a pivotable manner such that the lid 21 is fixable in its closed position. Pressure-medium cylinders also might be provided to pivot the lid 21 and the blocking means 24.

As is apparent, in particular from FIG. 1, the internal or inwardly projecting end 16 of the graphite pipe 14 is located at a distance 25 from the internal wall 26 of the converter formed by the working lining 7, which distance approximately corresponds to the thickness 27 of the working lining 7 of a newly lined converter 3 such that the graphite pipe 14 still is well supported at the end of a converter campaign when the working lining 7 has been burnt off almost completely. The temperature of the brick lining, in the region of the internal or inwardly projecting end 16 of the graphite pipe 14, ranges between about 1200° and 1300° C. such that slag penetrating into the bore 8 of the two perforated lining bricks 9, 10 cannot adhere to the lining bricks 9, 10 on account of the molten state of the slag in this temperature range, but flows off the same. The slag cannot deposit on the graphite pipe 14, either, whose temperature lies below the melting point of the slag. Slag possibly solidifying in the interior 15 of the pie 14 is readily removable by a hand scraper, hardly adhering to the pipe 14.

Figure 3:
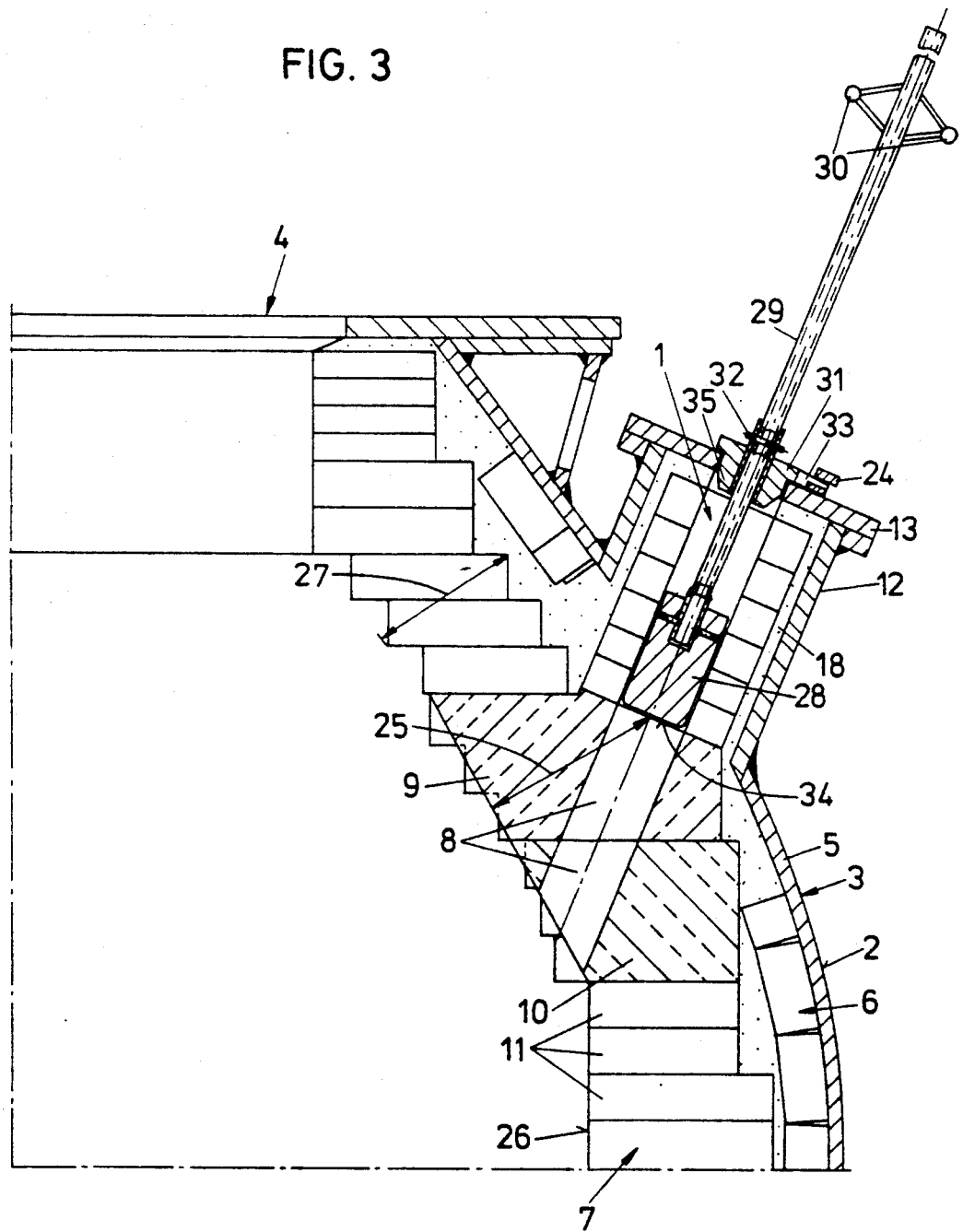
FIGS. 3, 4 and 5 depict further embodiments in illustrations analogous to FIG. 1.

According to the embodiment illustrated in FIG. 3, the refractory working lining 7 of the converter is led as far as to the front plate 13 of the socket 12 and is pierced to form of a probe opening 1. According to this embodiment, the adherence of slag is prevented by a stopper 28 of graphite. This stopper is fastened to the end of a guide rod 29. The guide rod 29 serves to remove the stopper from the bore 8, or to introduce it into the same, manually. For this purpose, the guide rod is provided with handles 30. It is also possible to provide a pressure medium cylinder for removing and inserting the stopper 28, instead of manual actuation.

Figure 2:
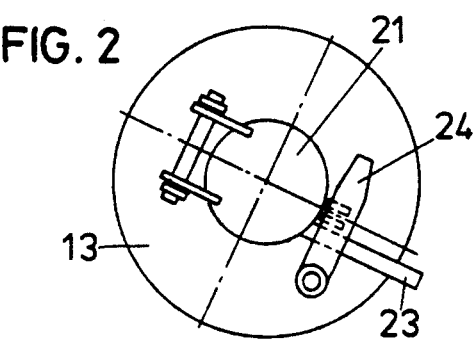
FIG. 2 is a top view of FIG. 1 in the direction of arrow II.

A lid 31 is movably arranged on the guide rod 29 for closing the probe opening 1. It may be fixed on the guide rod 29 at various distances from the stopper by a split-pin 32 or an adjustment screw. The lid 31 is provided with a projection 33 that maybe overlapped by a locking device 24 similar to the locking device illustrating in FIGS. 1 and 2 such that the lid 31 is fixed on the front plate 13 of the socket 12. Thus, the stopper 28 is fixed in the interior 8 of the probe opening 1, keeping its place during pivoting of the converter.

The lid 31, thus, serves as a stop for the stopper 28 to maintain a predetermined position in the interior 8 of the probe opening 1. As is apparent from FIG. 3, the front face 34 of the stopper 28 is at a distance 25 from the internal wall 26, that corresponds approximately to the thickness 27 of the working lining 7. Also in this case, the temperature on the front face 34 of the stopper within the probe opening amounts to about 1200° to 1300° C. such that no adherence of slag will occur. For the purpose of centering the guide rod 29, the lid 31 comprises a centering projection 35 projecting into the interior 8 of the probe opening 1 and whose external diameter is dimensioned to be only slightly larger than the internal diameter of the probe opening 1.

Figure 4:
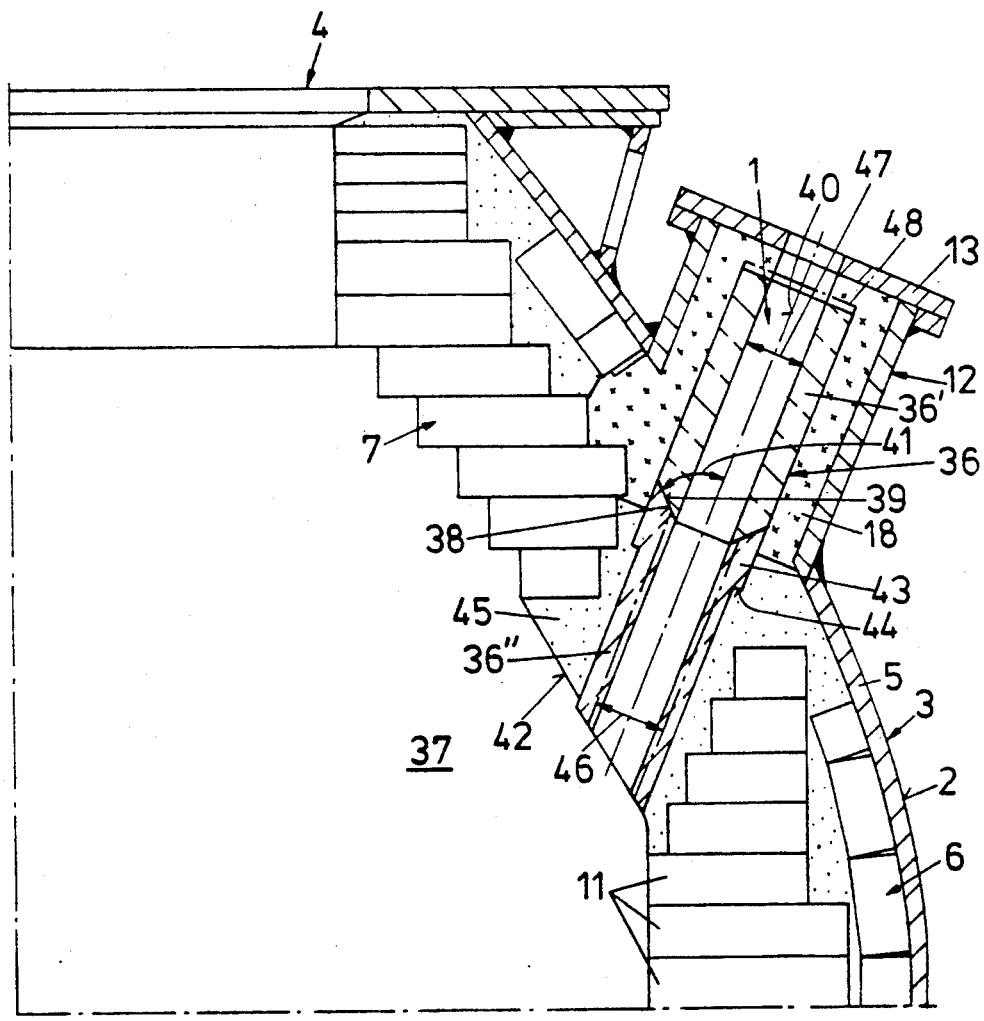

According to FIG. 4, a pipe 36 formed of graphite or a graphite/alumina mixture extends approximately over the entire length of the probe opening 1, reaching as far as to the internal space 37 of the metallurgical vessel 3. It is assembled of two sections 36', 36", however, for particularly long probe openings 1, it could also be composed of more than two sections.

The front faces 38, 39 provided on the ends of the pipe sections 36', 36" facing each other are designed as envelope of cone areas that is, conically bevelled, the pipe sections 36', 36", thus, being immobilized relative to each other in the direction transverse to the longitudinal axis 40 of the probe opening 1. The angle 41 of the generatrix of an envelope of cone area, or the angle of the conically shaped bevels with respect to the longitudinal axis 40 of a pipe section 36', 36" suitably ranges between 30° and 60°. In tests, a bevel angle 41° of 45° has proved particularly advantageous. If the angle 41 is too steep or too flat, parts of a pipe section 36', 36" may break off.

If a shift of the working lining 7 relative to the permanent lining 6 occurs—which shift is the largest on the side 42 facing the interior of the vessel the inner pie section 36", i.e., that pipe section 36" which reaches as far as to the internal space 37 of the metallurgical vessel 3, is moved relative to the outer pipe section 36' in a manner that an angular deviation of the axes of the pipe sections 36', 3641 results. On the other hand, displacement of the two pipe sections relative to each other transverse to the longitudinal axis 40 is not possible, because the adjacent front faces or conically shaped bevels 38, 39 of the pipe sections 36', 36" overlap or contact each other in male-female relationship in the direction transverse to the longitudinal axis 40, thus being supported on each other in this direction. Instead of the envelops of cone areas 38, 39, any other shapes of front faces may be employed, for instance, complementary spherical face, or a stepwise configuration of the front faces are feasible the end faces being matable in a male-female relationship when one end face is contacted with the other.

The pipe section 36' that lies next to the internal space of the metallurgical vessel 3, on its outwardly directed end, comprises an annular bead or flange 43 constituting a supporting shoulder 44, by which it is supported and retained on the refractory ramming mass 45 surrounding this pipe section 36".

In order to prevent even the slight protusion of an edge of the pipe section 36 ∝ if this pipe section 36" were moved by a drift of the working lining 7 relative to the permanent lining 6, the internal diameter 46 of the pipe section 36" arranged closer to the interior space 37 of the metallurgical vessel 3 suitably is dimensioned to be slightly larger than the internal diameter 47 of the adjacent pipe section 36' following outwardly, as is illustrated in dot-and-dash lines in FIG. 4. Suitably, the diameter difference amounts to about 2 cm.

The axial longitudinal displacement of the pipe sections 36', 36" may be enabled by a suitable clearance 48 in the outwardly extending region of the external pipe section 36', as is likewisely illustrated in dot-and-dash lines in FIG. 4. With the embodiment illustrated in FIG. 4, a lid 21 also may be provided, as is illustrated in FIG. 1.

Figure 5:
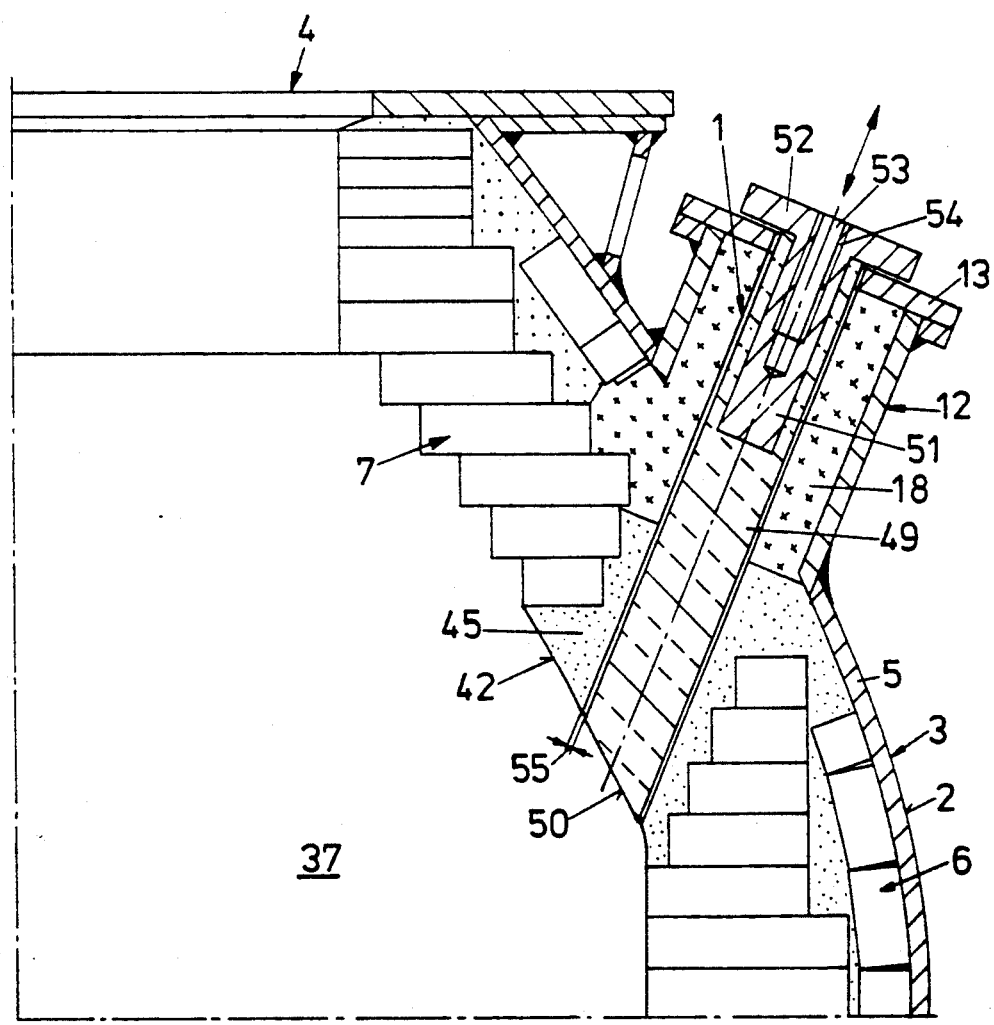

According to the embodiment illustrated in FIG. 5, the probe opening 1 is surrounded by refractory ramming mass 18, 45 over its entire length. A stopper 49 of graphite or of a graphite/alumina mixture is inserted in the probe opening 1, extending over the entire length of the probe opening 1 and whose inward end 50 matches or coincides with the internal side 42 of the vessel such that the stopper 49 basically does not form a projection on the internal side 42 of the metallurgical vessel 3.

On the outer end of the stopper 49 at the socket, a metal insert 51 is incorporated in the same, constituting an annular bead or flange 52 that overlaps the probe opening 1, thus maintaining the stopper 49 in its correct position by the annular bead or flange 52 abutting on the front plate 13 of the socket 12. A bore 53 is coaxially formed into the insert 51, having an internal thread 54 such that a manipulation device for removing the stopper 49 from, and inserting it into, the probe opening 1 is attachable thereto. The stopper 49 has a lateral play 55 relative to the probe opening 1, which preferably amounts to about 2.5% of the diameter of the probe opening 1.

With the embodiment illustrated in FIG. 5, the probe opening 1 could also be lined with a graphite pipe, as is illustrated in FIGS. 1, 3 and 4.

The pipe or the stopper may be made of pure graphite (degree of purity 99.9%). However, it is also possible to use a graphite/alumina mixture, which consists of 5 to 20% graphite, 30 to 60% $Al_2O_3$, the balance being fireclay, in the case of the stopper 28, and of 60 to 85% graphite, the balance being $Al_2O_3$ and fireclay, in the case of the pipe.

What we claim is:

1. In a metallurgical vessel comprised of an outer shell lined on its interior wall with a refractory brick lining and adapted for melting metal, said vessel having a probe opening therein of a length extending from the outer shell to the interior of said vessel for introducing a measuring and/or sampling probe therein, said probe opening entering said vessel through said brick lining along its longitudinal axis, the combination therewith of a probe opening stopper entering said probe opening and made of a material selected from the group consisting of graphite and a graphite/alumina mixture consisting essentially by weight of about 60% to 85% graphite, with the balance essentially alumina and fireclay.

2. A metallurgical vessel as set forth in claim 1, wherein said stopper has an internal-side end which reaches at least as far as into a region of said refractory brick lining having a temperature of about 1200° C.

3. A metallurgical vessel as set forth in claim 1, wherein said stopper has an internal-side end which maximally reaches as far as into a region of said refractory brick lining having a temperature of about 1300° C.

4. A metallurgical vessel as set forth in claim 1, further comprising a guide rod fastened to said stopper and a stop provided on said guide rod at a distance from said stopper, said stop abutting on the shell of said metallurgical vessel.

5. A metallurgical vessel as set forth in claim 4, wherein said stop is designed to be displaceable along said guide rod and fixable on said guide rod.

6. A metallurgical vessel as set forth in claim 4, wherein said stop is designed as a lid.

7. A metallurgical vessel as set forth in claim 4, further comprising a centering projection provided on said stop on its side facing said vessel internal space.

8. A metallurgical vessel as set forth in claim 4, further comprising a blocking means for fixing said stop on the shell of said metallurgical vessel.

9. A metallurgical vessel as set forth in claim 8, further comprising a pressure medium cylinder for actuating said blocking means.

10. A metallurgical vessel as set forth in claim 4, further comprising a pressure medium cylinder for actuating said guide rod.

11. A metallurgical vessel as set forth in claim 1, wherein said stopper extends over the entire length of said probe opening.

12. A metallurgical vessel as set forth in claim 11, wherein said stopper has a stopper end facing the internal side of said vessel and having a front face matching said internal side of said vessel.

13. A metallurgical vessel as set forth in claim 11, wherein said stopper has a stopper end reaching outwardly and including a metal insert, said metal insert having a coupling means adapted for attachment of a stopper manipulation means.

14. A metallurgical vessel as set forth in claim 13, further comprising an annular bead provided on said metal insert in a manner overlapping said probe opening.

15. A metallurgical vessel as set forth in claim 11, wherein said stopper has an external diameter dimensioned to be smaller than said internal diameter of said probe opening by about 3 to 15%.

16. A metallurgical vessel as set forth in claim 11, wherein said stopper has an external diameter dimensioned to be smaller than said internal diameter of said probe opening by about 5%.

* * * * *